(12) United States Patent
Lalleman et al.

(10) Patent No.: US 8,801,808 B2
(45) Date of Patent: Aug. 12, 2014

(54) DYE COMPOSITION COMPRISING BENZYL ALCOHOL, A MONOALCOHOL AND A PARTICULAR DIRECT DYE

(75) Inventors: Boris Lalleman, Paris (FR); Alain Lagrange, Coupvray (FR)

(73) Assignee: L'oreal, Paris (FR)

( * ) Notice: Subject to any disclaimer, the term of this patent is extended or adjusted under 35 U.S.C. 154(b) by 0 days.

(21) Appl. No.: 13/995,662

(22) PCT Filed: Dec. 19, 2011

(86) PCT No.: PCT/EP2011/073230
§ 371 (c)(1),
(2), (4) Date: Jun. 19, 2013

(87) PCT Pub. No.: WO2012/084817
PCT Pub. Date: Jun. 28, 2012

(65) Prior Publication Data
US 2013/0269120 A1   Oct. 17, 2013

Related U.S. Application Data

(60) Provisional application No. 61/434,072, filed on Jan. 19, 2011, provisional application No. 61/434,527, filed on Jan. 20, 2011.

(30) Foreign Application Priority Data

Dec. 20, 2010  (FR) .................................... 10 60797
Dec. 20, 2010  (FR) .................................... 10 60799

(51) Int. Cl.
*A61Q 5/10* (2006.01)
*C09B 1/00* (2006.01)

(52) U.S. Cl.
USPC ......... 8/405; 8/426; 8/643; 552/247; 552/302

(58) Field of Classification Search
CPC .. A61K 8/34; A61K 8/413; A61K 2800/4322
USPC ..................... 8/405, 426, 643; 552/247, 302
See application file for complete search history.

(56) References Cited

U.S. PATENT DOCUMENTS

| | | | |
|---|---|---|---|
| 3,528,972 | A | 9/1970 | Kalopissis et al. |
| 4,137,180 | A | 1/1979 | Naik et al. |
| 4,874,554 | A | 10/1989 | Lange et al. |
| 5,708,151 | A | 1/1998 | Möckli |
| 8,066,782 | B2 | 11/2011 | Leduc et al. |
| 8,083,809 | B2 | 12/2011 | Leduc et al. |
| 8,105,394 | B2 | 1/2012 | Leduc et al. |
| 2006/0031999 | A1 | 2/2006 | De Boni et al. |
| 2009/0282624 | A1 | 11/2009 | De Boni |
| 2011/0041261 | A1 | 2/2011 | Leduc et al. |
| 2011/0041262 | A1 | 2/2011 | Leduc et al. |
| 2011/0041263 | A1 | 2/2011 | Leduc et al. |

FOREIGN PATENT DOCUMENTS

| | | |
|---|---|---|
| EP | 0 714 954 A2 | 6/1996 |
| EP | 1 820 826 A1 | 8/2007 |
| FR | 2 874 178 A1 | 2/2006 |
| FR | 2 925 049 A1 | 6/2009 |
| FR | 2 925 054 A1 | 6/2009 |
| FR | 2 925 055 A1 | 6/2009 |
| FR | 2 925 056 A1 | 6/2009 |
| FR | 2 928 085 A1 | 9/2009 |
| WO | 95/01772 A1 | 1/1995 |
| WO | 95/15144 A1 | 6/1995 |
| WO | WO 2009/077393 A1 * | 6/2009 ............... A61Q 5/10 |

OTHER PUBLICATIONS

STIC Search Report dated Jul. 31, 2013.*
Meylan, William M., et al., "Atom/Fragment Contribution Method for Estimating Octanol-Water Partition Coefficients," Journal of Pharmaceutical Sciences, vol. 84, No. 1, Jan. 1995, pp. 83-92.

* cited by examiner

*Primary Examiner* — Eisa Elhilo
(74) *Attorney, Agent, or Firm* — The Marbury Law Group, PLLC

(57) ABSTRACT

One subject of the present invention is a dye composition comprising benzyl alcohol, at least one C1-C4 monoalcohol and at least one anthraquinone direct dye of formula (I) or azomethine direct dye of formula (II). The composition of the invention makes it possible to obtain colorings that are intense and resistant.

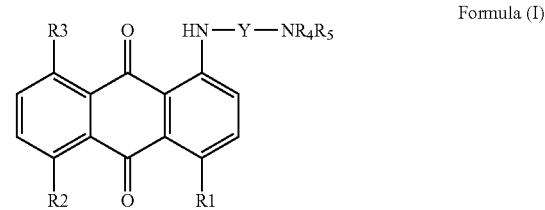

Formula (I)

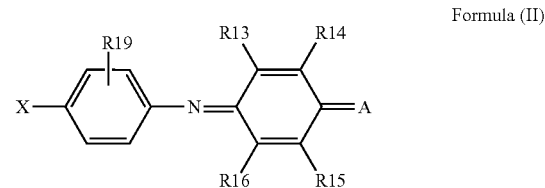

Formula (II)

21 Claims, No Drawings

DYE COMPOSITION COMPRISING BENZYL ALCOHOL, A MONOALCOHOL AND A PARTICULAR DIRECT DYE

This is a national stage application of PCT/EP2011/073230, filed internationally on Dec. 19, 2011, which claims priority to U.S. Provisional Application Nos. 61/434,072, filed on Jan. 19, 2011 and 61/434,527, filed on Jan. 20, 2011; as well as French Application Nos. FR 1060797, filed on Dec. 20, 2010 and FR 1060799, filed on Dec. 20, 2010.

One subject of the invention is a composition for dyeing keratin fibres using one particular anthraquinone dye.

Two major methods for dyeing human keratin fibres, and in particular the hair, are known.

The first, known as oxidation dyeing or permanent dyeing, consists in using one or more oxidation dye precursors, more particularly one or more oxidation bases optionally combined with one or more couplers.

Oxidation bases are usually selected from ortho- or para-phenylenediamines, ortho- or para-aminophenols, and heterocyclic compounds. These oxidation bases are colourless or weakly coloured compounds, which, when combined with oxidizing products, can give rise via a process of oxidative condensation to coloured species, which remain trapped within the fibre.

The shades obtained with these oxidation bases are often varied by combining them with one or more couplers, these couplers being chosen especially from aromatic meta-diamines, meta-aminophenols, meta-diphenols and certain heterocyclic compounds, such as indole compounds.

The variety of molecules used as oxidation bases and couplers allows a wide range of colours to be obtained.

The second dyeing method, known as direct dyeing or semipermanent dyeing, comprises the application of direct dyes, which are coloured and colouring molecules that have affinity for fibres. Given the nature of the molecules used, they tend rather to remain on the surface of the fibre and penetrate relatively little into the fibre, when compared with the small molecules of oxidation dye precursors.

The direct dyes generally used are chosen from nitrobenzene, anthraquinone, nitropyridine, azo, methine, azomethine, xanthene, acridine, azine and triarylmethane direct dyes. The chemical species used may be nonionic, anionic (acidic dyes) or cationic (basic dyes).

The majority of the direct dyes used have sufficient solubility in aqueous medium, and numerous dye supports suitable for receiving them now exist.

It is in particular known, for example from document FR 2928085, to use dye compositions comprising dyes, benzyl alcohol and ethanol. A dye composition comprising an anthraquinone dye in an aqueous-alcoholic mixture is also known from document FR 2874178.

It is furthermore known to use, for dyeing hair, monoamino- or diamino-anthraquinone dyes, in particular from documents U.S. Pat. No. 3,528,972, U.S. Pat. No. 3,477,483 and EP 1820826.

Nonionic azomethine dyes, and in particular nonionic indoamine dyes are, however, not very soluble and are difficult to use.

Documents FR 2925055, FR 2925056, FR 2925054 and FR 2925049 describe dye compositions comprising azomethine dyes, benzyl alcohol and a monoalcohol.

However, the compositions that are already known do not make it possible to obtain shades that are sufficiently intense or chomatic and resistant on the hair, preferably in the blue to violet shades.

One of the objectives of the present invention is therefore to propose compositions that have satisfactory dyeing properties, especially insofar as they make it possible to obtain shades that are particularly intense and/or chromatic, uniform in colouring between the end and the root of the hair and that are more particularly long-lasting with respect to shampooing operations and/or the light.

A second objective of the present invention is to propose compositions that have satisfactory dyeing properties, especially insofar as they make it possible to obtain blue to violet colourings that are strong and long-lasting with respect to shampooing operations and/or the light and uniform between the end and the root of the hair.

This objective is achieved with the present invention, one subject of which is a composition for dyeing keratin fibres which comprises benzyl alcohol, at least one C1-C4 monoalcohol and at least one direct dye of formula (I) or (II), or a salt, hydrate or halohydrate thereof, and in which the monoalcohol(s)/benzyl alcohol weight ratio is less than or equal to 6:

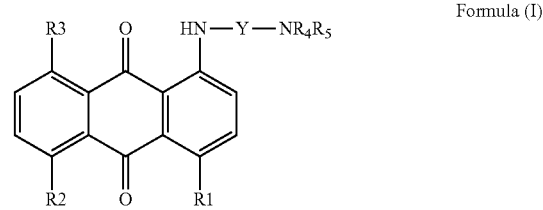

Formula (I)

in which Y represents a divalent alkylene radical comprising from 1 to 8 carbon atoms and $R_4$ and $R_5$ each separately represent a hydrogen atom, an alkyl or hydroxyalkyl radical comprising from 1 to 8 carbon atoms; R1 represents a hydrogen atom or a hydroxyl radical; R2 and R3 each separately represent a hydrogen atom or an $NH_2$ radical.

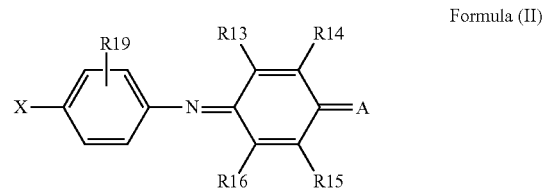

Formula (II)

in which:
X represents the groups —OH, NH2, NHR11 or NHR12 or else NR11R12 with R11 and R12 representing:
 a C1-C8 alkyl group, optionally substituted by an —OH group or an amino group substituted by a radical comprising at least one C6-C20 aromatic ring, R13, R14, R15 and R16 each independently represent:
a hydrogen atom;
a halogen atom;
a hydroxyl group;
an optionally substituted, linear or branched C1-C8 alkoxy or alkyl group;
an NH2 or NHR17 group with R17 denoting a (C1-C4) alkoxycarbonylamino radical or a C6-C20 aromatic radical optionally substituted by one or more groups chosen from amino, hydroxyl, C1-C4 alkyl, (C1-C4) dialkylamino, (C1-C4)alkylhydroxy(C1-C4)alkylamino or dihydroxy(C1-C4)alkylamino groups;
A represents an oxygen atom or NH, or NR18 with R18 representing a C1-C4 alkyl radical; and R19 represents a hydrogen atom or a C1-C8 alkyl radical.

The composition of the invention makes it possible to obtain a colouring of the fibres that is strong and resistant to external agents, especially the light, and to repeated washing operations.

Within the context of the invention, the term "at least one" associated with an element of the composition means one or more of these elements.

According to one embodiment of the invention, the dyes of formula (I) or (II) have a log P of greater than 1.

Within the context of the invention, the log P value conventionally represents the partition coefficient of the dye between octanol and water. The log P may be calculated according to the method described in the article by Meylan and Howard "*Atom/fragment contribution method for estimating octanol-water partition coefficient*', J. Pharm. Sci. 84, 83-92 (1995). This value may also be calculated by means of numerous software packages available on the market, which determine the log P as a function of the structure of a molecule. An example that may be mentioned is the Epiwin software from the United States Environmental Protection Agency.

According to one particular embodiment, the log P of the dye of use in the invention is greater than 4.

In the formula (I) defined previously, the anthraquinone dyes are preferably such that the R4 and R5 radicals preferably independently represent a C1-C4 alkyl radical. Preferably, Y comprises from 1 to 4 carbon atoms.

Examples that may be mentioned include the dyes of formula (I) below, these dyes being particularly preferred:

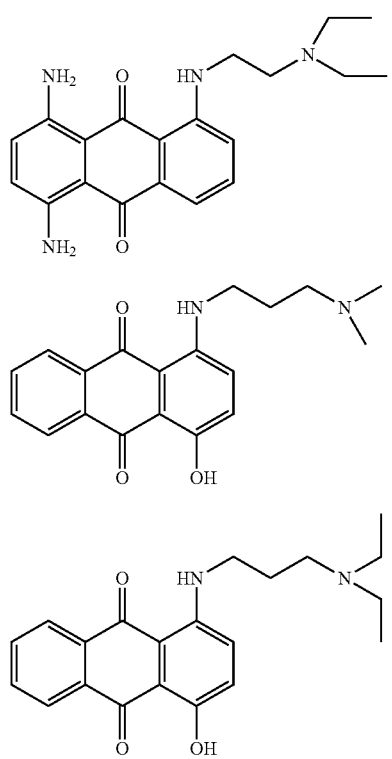

The direct dye(s) of formula (I) may be present in the composition in amounts that range from 0.001% to 10%, preferably between 0.1% and 5%, by weight approximately of the total weight of the composition.

In formula (II), the azomethine dyes defined previously are preferably those in which R13 and R15 represent a hydrogen atom.

In this formula (II), R16 preferably represents an $NH_2$ group; hydroxyl; an NHR17 group with R17 denoting a phenyl group substituted by an amino or di(C1-C4)alkylamino, dihydroxy(C1-C4)alkylamino or (C1-C4)alkylhydroxy(C1-C4)alkylamino group; or an ethoxycarbonylamino group.

In this formula (II), R14 preferably represents a group chosen from alkoxy, $NH_2$, hydroxyphenylamino and aminophenylamino groups, the phenyl radical of which is optionally substituted by a $C_{104}$ alkyl.

In this formula (II), X preferably represents a hydroxyl; amino; di(C1-C4)alkylamino; (C1-C4)alkylhydroxy(C1-C4) alkylamino; (C1-C4)alkylbenzoylamino(C1-C4)alkylamino; or dihydroxy(C1-C4)alkylamino group.

In this formula (II), A preferably represents an oxygen atom or an NH group.

In this formula (II), R19 preferably represents a hydrogen atom or a methyl radical.

Examples that may be mentioned include the dyes of formula (II) below, these dyes being particularly preferred:

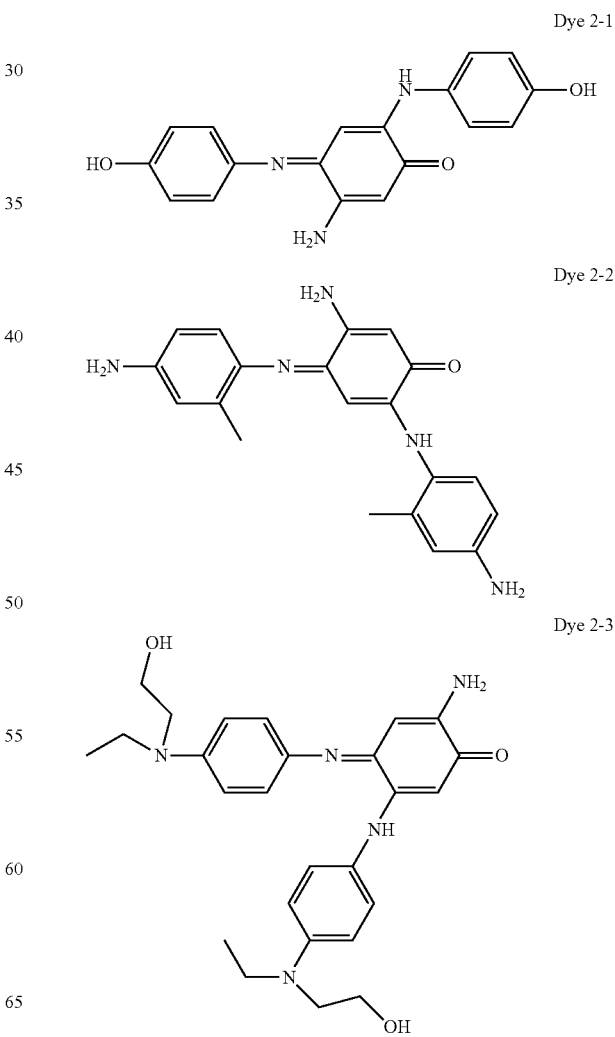

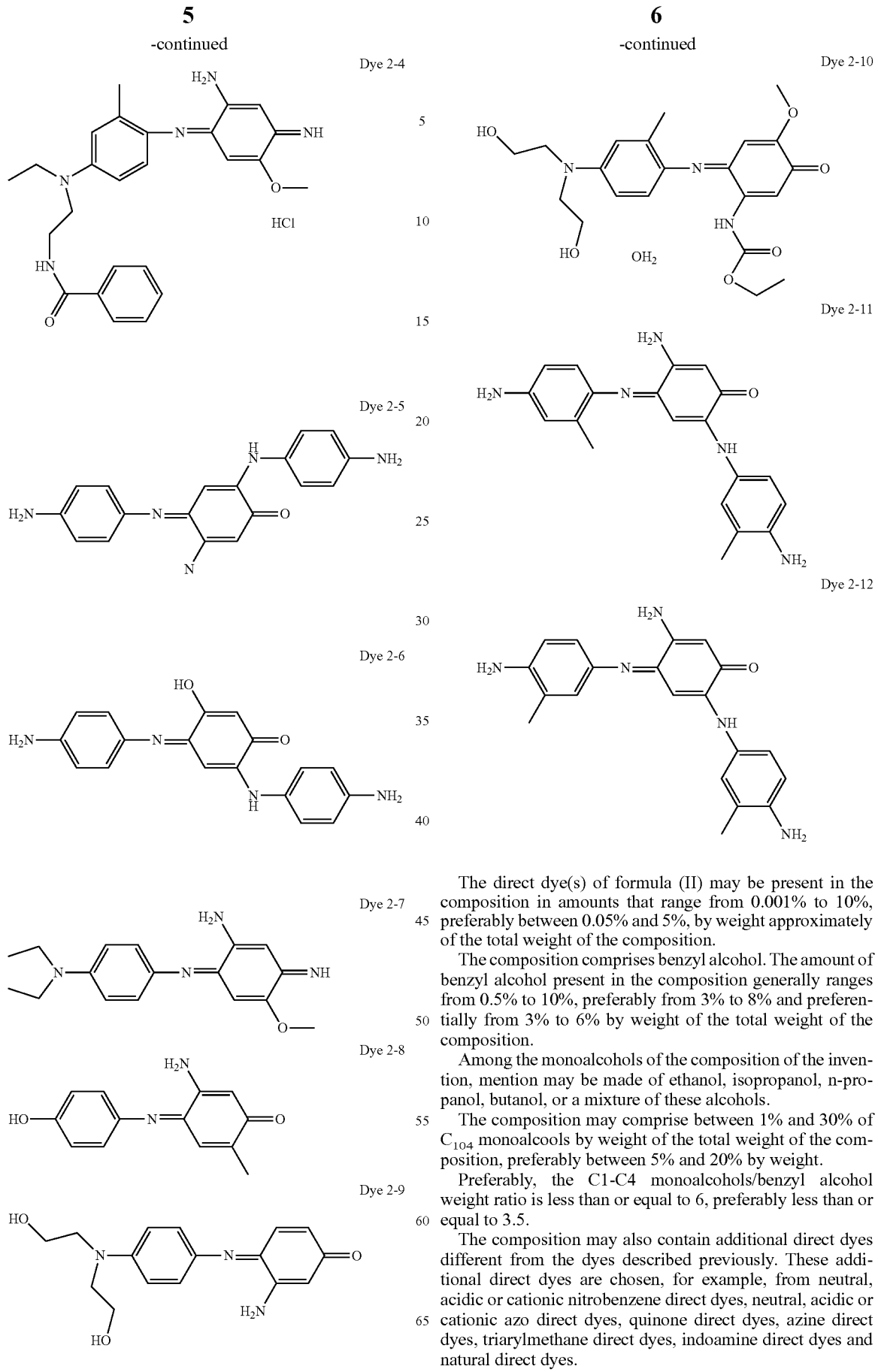

The direct dye(s) of formula (II) may be present in the composition in amounts that range from 0.001% to 10%, preferably between 0.05% and 5%, by weight approximately of the total weight of the composition.

The composition comprises benzyl alcohol. The amount of benzyl alcohol present in the composition generally ranges from 0.5% to 10%, preferably from 3% to 8% and preferentially from 3% to 6% by weight of the total weight of the composition.

Among the monoalcohols of the composition of the invention, mention may be made of ethanol, isopropanol, n-propanol, butanol, or a mixture of these alcohols.

The composition may comprise between 1% and 30% of $C_{1O4}$ monoalcools by weight of the total weight of the composition, preferably between 5% and 20% by weight.

Preferably, the C1-C4 monoalcohols/benzyl alcohol weight ratio is less than or equal to 6, preferably less than or equal to 3.5.

The composition may also contain additional direct dyes different from the dyes described previously. These additional direct dyes are chosen, for example, from neutral, acidic or cationic nitrobenzene direct dyes, neutral, acidic or cationic azo direct dyes, quinone direct dyes, azine direct dyes, triarylmethane direct dyes, indoamine direct dyes and natural direct dyes.

Among the benzene direct dyes, mention may be made, in a nonlimiting manner, of the following compounds:
1,4-diamino-2-nitrobenzene
1-amino-2-nitro-4-β-hydroxyethylaminobenzene
1-amino-2-nitro-4-bis(β-hydroxyethyl)aminobenzene
1,4-bis(β-hydroxyethylamino)-2-nitrobenzene
1-β-hydroxyethylamino-2-nitro-4-bis(β-hydroxyethylamino)benzene
1-β-hydroxyethylamino-2-nitro-4-aminobenzene
1-β-hydroxyethylamino-2-nitro-4-(ethyl)(β-hydroxyethyl)aminobenzene
1-amino-3-methyl-4-β-hydroxyethylamino-6-nitrobenzene
1-amino-2-nitro-4-β-hydroxyethylamino-5-chlorobenzene
1,2-diamino-4-nitrobenzene
1-amino-2-β-hydroxyethylamino-5-nitrobenzene
1,2-bis(β-hydroxyethylamino)-4-nitrobenzene
1-amino-2-tris(hydroxymethyl)methylamino-5-nitrobenzene
1-hydroxy-2-amino-5-nitrobenzene
1-hydroxy-2-amino-4-nitrobenzene
1-hydroxy-3-nitro-4-aminobenzene
1-hydroxy-2-amino-4,6-dinitrobenzene
1-β-hydroxyethyloxy-2-β-hydroxyethylamino-5-nitrobenzene
1-methoxy-2-β-hydroxyethylamino-5-nitrobenzene
1-β-hydroxyethyloxy-3-methylamino-4-nitrobenzene
1-β,γ-dihydroxypropyloxy-3-methylamino-4-nitrobenzene
1-β-hydroxyethylamino-3-methyl-2-nitrobenzene
1-β-aminoethylamino-5-methoxy-2-nitrobenzene
1-hydroxy-2-chloro-6-ethylamino-4-nitrobenzene
1-hydroxy-2-chloro-6-amino-4-nitrobenzene
1-hydroxy-6-bis(β-hydroxyethyl)amino-3-nitrobenzene
1-β-hydroxyethylamino-2-nitrobenzene
1-hydroxy-4-β-hydroxyethylamino-3-nitrobenzene.

Among the azo direct dyes, mention may be made of the cationic azo dyes described in patent applications WO 95/15144, WO 95/01772 and EP 714 954, the content of which forms an integral part of the invention.

Among these compounds, mention may be made very particularly of the following dyes:
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulphate.

Among the azo direct dyes, mention may also be made of the following dyes, described in the Colour Index International 3rd edition:
Acid Yellow 9
Acid Black 1
Basic Red 22
Basic Red 76
Basic Yellow 57
Basic Brown 16
Acid Yellow 36
Acid Orange 7
Acid Red 33
Acid Red 35
Basic Brown 17
Acid Yellow 23
Acid Orange 24

Mention may also be made of 1-(4'-aminodiphenylazo)-2-methyl-4-bis(β-hydroxyethyl)aminobenzene and 4-hydroxy-3-(2-methoxyphenylazo)-1-naphthalenesulphonic acid.

Among the quinone direct dyes, mention may be made of the following dyes:
Acid Violet 43
Acid Blue 62
Basic Blue 22
Basic Blue 99
and also the following compounds:
1-N-methylmorpholiniumpropylamino-4-hydroxyanthraquinone
1-aminopropylamino-4-methylaminoanthraquinone
1-aminopropylaminoanthraquinone
5-β-hydroxyethyl-1,4-diaminoanthraquinone
2-aminoethylaminoanthraquinone
1,4-bis(β,γ-dihydroxypropylamino)anthraquinone.

Among the azine dyes, mention may be made of the following compounds:
Basic Blue 17
Basic Red 2.

Among the triarylmethane dyes, mention may be made of the following compounds:
Basic Green 1
Acid blue 9
Basic Violet 3
Basic Violet 14
Basic Blue 7
Acid Violet 49
Basic Blue 26
Acid Blue 7

Among the natural direct dyes that can be used according to the invention, mention may be made of lawsone, juglone, alizarin, purpurin, carminic acid, kermesic acid and spinulosin. Extracts or decoctions containing these natural dyes and especially henna-based poultices or extracts, may also be used.

When this composition comprises direct dyes other than those of formula (I), the composition may contain up to 20% of direct dyes. According to this particular embodiment, the composition of the invention preferably comprises a total amount of additional direct dyes between 0.001% and 10% by weight approximately.

The composition may furthermore contain oxidation bases and couplers conventionally used for oxidation dyeing.

By way of example, mention may be made of para-phenylenediamines, bis(phenyl)alkylenediamines, para-aminophenols, ortho-aminophenols and heterocyclic bases, and the addition salts thereof.

The couplers are for example meta-phenylenediamine couplers, meta-aminophenol couplers, meta-diphenol couplers, naphthalene-based couplers and heterocyclic couplers, and the addition salts thereof.

When they are present, the bases and couplers are each generally present in an amount of between 0.001% and 10% by weight approximately of the total weight of the dye composition, preferably between 0.005% and 6%.

The composition may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

These above adjuvants are generally present in an amount, for each of them, of between 0.01% and 20% by weight relative to the weight of the composition.

According to one particular embodiment, the composition of the invention contains one or more cationic surfactants.

For the purposes of the present invention, the term "cationic surfactant" means a surfactant that is positively charged when it is contained in the composition according to the invention. This surfactant may bear one or more positive permanent charges or may contain one or more cationizable functions in the composition according to the invention.

As examples of cationic surfactants that can be used in the cosmetic composition, mention may be made especially of optionally polyoxyalkylenated primary, secondary or tertiary fatty amines, or salts thereof, and quaternary ammonium salts, and mixtures thereof.

Fatty amines generally comprise at least one $C_8$-$C_{30}$ hydrocarbon-based chain. Among the fatty amines that can be used according to the invention, an example that may be mentioned is stearyl amidopropyl dimethylamine.

Examples of quaternary ammonium salts that may especially be mentioned include:
those that have the general formula (A) below:

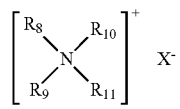

in which the $R_8$ to $R_{11}$ radicals, which may be identical or different, represent a linear or branched aliphatic radical comprising from 1 to 30 carbon atoms, or an aromatic radical, such as aryl or alkylaryl, at least one of the $R_8$ to $R_{11}$ radicals comprising from 8 to 30 carbon atoms, preferably from 12 to 24 carbon atoms. The aliphatic radicals may comprise heteroatoms especially such as oxygen, nitrogen, sulphur and halogens.

The aliphatic radicals are, for example, chosen from alkyl, alkenyl, alkoxy, polyoxy($C_2$-$C_6$)alkylene, alkylamide, ($C_{12}$-$C_{22}$)alkylamido($C_2$-$C_6$)alkyl, ($C_{12}$-$C_{22}$)alkyl acetate or hydroxyalkyl radicals comprising approximately from 1 to 30 carbon atoms; $X^-$ is an anion chosen from the group of the halides, phosphates, acetates, lactates, ($C_2$-$C_6$)alkyl sulphates, or alkyl or alkylaryl sulphonates;

quaternary ammonium salts of imidazoline, such as, for example, those of formula (B) below:

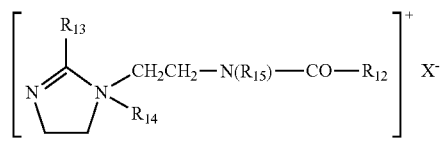

in which $R_{12}$ represents an alkenyl or alkyl radical comprising from 8 to 30 carbon atoms, for example derived from tallow fatty acids, $R_{13}$ represents a hydrogen atom, a $C_1$-$C_4$ alkyl radical or an alkenyl or alkyl radical comprising from 8 to 30 carbon atoms, $R_{14}$ represents a $C_1$-$C_4$ alkyl radical, $R_{15}$ represents a hydrogen atom or a $C_1$-$C_4$ alkyl radical and $X^-$ is an anion chosen from the group of the halides, phosphates, acetates, lactates, alkyl sulphates, or alkyl or alkylaryl sulphonates. Preferably, $R_{12}$ and $R_{13}$ denote a mixture of alkenyl or alkyl radicals comprising from 12 to 21 carbon atoms, for example derived from tallow fatty acids, $R_{14}$ denotes a methyl radical and $R_{15}$ denotes a hydrogen atom. Such a product is sold, for example, under the name Rewoquat® W 75 by the company Rewo;

quaternary diammonium or triammonium salts, in particular of formula (C):

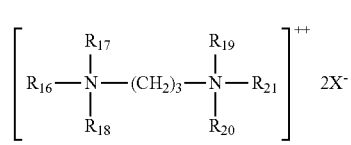

in which $R_{16}$ denotes an alkyl radical containing approximately from 16 to 30 carbon atoms, which is optionally hydroxylated and/or interrupted with one or more oxygen atoms and optionally branched, $R_{17}$ is selected from an alkyl radical containing from 1 to 4 carbon atoms or a group $(R_{16a})(R_{17a})(R_{18})N^+$—$(CH_2)_3$—, $R_{16a}$, $R_{17a}$, $R_{18a}$, $R_{18}$, $R_{19}$, $R_{20}$ and $R_{21}$, which may be identical or different, are selected from hydrogen or an alkyl radical containing from 1 to 4 carbon atoms, and $X^-$ is an anion selected from the group of halides, acetates, phosphates, nitrates and methyl sulphates. Such compounds are, for example, Finquat CT-P, available from the company Finetex (Quaternium 89), and Finquat CT, available from the company Finetex (Quaternium 75), quaternary ammonium salts containing at least one ester function, such as those of formula (IV) below:

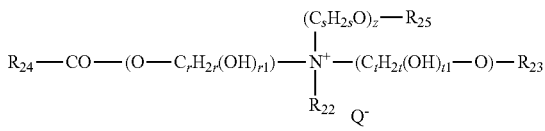

in which:
$R_{22}$ is chosen from $C_1$-$C_6$ alkyl radicals and $C_1$-$C_6$ hydroxyalkyl or dihydroxyalkyl radicals;
$R_{23}$ is chosen from:
the radical

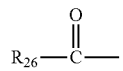

radicals $R_{27}$, which are linear or branched, saturated or unsaturated $C_1$-$C_{22}$ hydrocarbon-based radicals;
the hydrogen atom;
$R_{25}$ is chosen from:
the radical

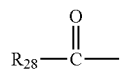

radicals $R_{29}$, which are linear or branched, saturated or unsaturated $C_1$-$C_6$ hydrocarbon-based radicals;
the hydrogen atom;
$R_{24}$, $R_{26}$ and $R_{28}$, which are identical or different, are selected from linear or branched, saturated or unsaturated $C_7$-$C_{21}$ hydrocarbon-based radicals;

r, s and t, which may be identical or different, are integers ranging from 2 to 6;

r1 and t1, which may be identical or different, are 0 or 1 and r2+r1=2r and t1+t2=2t;

y is an integer ranging from 1 to 10;

x and z, which may be identical or different, are integers ranging from 0 to 10;

$X^-$ is a simple or complex, organic or inorganic anion; with the proviso that the sum x+y+z has a value from 1 to 15, that when x is equal to 0 then $R_{23}$ denotes $R_{27}$ and that when z is equal to 0 then $R_{25}$ denotes $R_{29}$;

$Q^-$ represents an anionic counterion.

The alkyl radicals $R_{22}$ may be linear or branched, and more particularly linear.

Preferably, $R_{22}$ denotes a methyl, ethyl, hydroxyethyl or dihydroxypropyl radical and more particularly a methyl or ethyl radical.

Advantageously, the sum x+y+z has a value from 1 to 10.

When $R_{23}$ is a hydrocarbon-based radical $R_{27}$, it may be long and have from 12 to 22 carbon atoms, or may be short and have from 1 to 3 carbon atoms.

When $R_{25}$ is a hydrocarbon-based radical $R_{29}$, it has preferably 1 to 3 carbon atoms.

Advantageously, $R_{24}$, $R_{26}$ and $R_{28}$, which are identical or different, are selected from saturated or unsaturated, linear or branched $C_{11}$-$C_{21}$ hydrocarbon-based radicals, and more particularly from saturated or unsaturated, linear or branched, $C_{11}$-$C_{21}$ alkyl and alkenyl radicals.

Preferably, x and z, which may be identical or different, are equal to 0 or 1.

Advantageously, y is equal to 1.

Preferably, r, s and t, which may be identical or different, are equal to 2 or 3, and even more particularly are equal to 2.

The anion $X^-$ is preferably a halide (chloride, bromide or iodide) or an alkyl sulphate, more particularly methyl sulphate. However, use may be made of methanesulphonate, phosphate, nitrate, tosylate, an anion derived from an organic acid, such as acetate or lactate, or any other anion compatible with the ammonium containing an ester function.

The anion $X^-$ is even more particularly chloride or methyl sulphate.

Use is made more particularly, in the composition according to the invention, of the ammonium salts of formula (IV) in which:

$R_{22}$ denotes a methyl or ethyl radical;

x and y are equal to 1;

z is equal to 0 or 1;

r, s and t are equal to 2;

$R_{23}$ is chosen from:

the radical

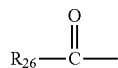

methyl, ethyl or $C_{14}$-$C_{22}$ hydrocarbon-based radicals;

the hydrogen atom;

$R_{25}$ is chosen from:

the radical

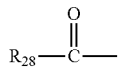

the hydrogen atom;

$R_{24}$, $R_{26}$ and $R_{28}$, which are identical or different, are chosen from linear or branched, saturated or unsaturated $C_{13}$-$C_{17}$ hydrocarbon-based radicals and preferably from linear or branched, saturated or unsaturated $C_{13}$-$C_{17}$ alkyl and alkenyl radicals.

The hydrocarbon-based radicals are advantageously linear.

Examples that may be mentioned include the compounds of formula (IV) such as the diacyloxyethyldimethylammonium, diacyloxyethyl-hydroxyethyl methylammonium, monoacyloxyethyldihydroxyethylmethyl-ammonium, triacyloxyethylmethylammonium and monoacyloxyethylhydroxyethyl-dimethylammonium salts (chloride or methyl sulphate in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, triisopropanolamine, alkyldiethanolamine or alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl (preferably methyl or ethyl)halide, a dialkyl (preferably dimethyl or diethyl)sulphate, methyl methanesulphonate, methyl para-toluenesulphonate, glycol chlorohydrin or glycerol chlorohydrin.

Such compounds are, for example, sold under the names Dehyquart® by the company Henkel, Stepanquat® by the company Stepan, Noxamium® by the company Ceca or Rewoquat® WE 18 by the company Rewo-Witco.

The composition according to the invention preferably contains a mixture of quaternary ammonium monoester, diester and triester salts with a weight majority of diester salts.

It is also possible to use the ammonium salts containing at least one ester function that are described in U.S. Pat. No. 4,874,554 and U.S. Pat. No. 4,137,180.

Preferably, the cosmetic composition according to the invention comprises one or more cationic surfactants chosen from the quaternary ammonium salts corresponding to formula (A).

Preference is given, among the quaternary ammonium salts of formula (A), on the one hand, to tetraalkylammonium chlorides, such as, for example, dialkyldimethylammonium or alkyltrimethylammonium chlorides in which the alkyl radical comprises approximately from 12 to 22 carbon atoms, in particular behenyltrimethylammonium chloride, distearyldimethylammonium chloride, cetyltrimethylammonium chloride or benzyldimethylstearylammonium chloride, or else, on the other hand, to distearoylethylhydroxyethylmethylammonium methosulphate, dipalmitoylethylhydroxyethylammonium methosulphate, distearoylethylhydroxyethylammonium methosulphate or hydroxyethyloleyldimethyl ammonium chloride, or else, finally, to palmityl-amidopropyltrimethylammonium chloride or stearamidopropyldimethyl(myristyl acetate)ammonium chloride, sold under the name Ceraphyl® 70 by Van Dyk.

Among all the cationic surfactants that may be present in the composition according to the invention, cationic surfactants from among cetyltrimethylammonium (INCI: cetrimonium), behenyltrimethylammonium (INCI: behentrimonium), dipalmitoyl-ethylhydroxyethylmethylammonium, distearoylethylhydroxyethylmethylammonium, methyl(C9-C19)alkyl(C10-C20)alkylamidoethylimidazolium and stearamidopropyl-dimethylamine salts (chloride or methosulphate), and the stearamidopropyldimethyl-ammonium salt, and mixtures thereof, are preferably chosen.

When they are present, the amount of the cationic surfactant(s) preferably ranges from 0.01% to 20% by weight and better still from 0.1% to 5% by weight relative to the total weight of the composition.

For the dyeing of human keratin fibres, the dyeing medium is a cosmetic medium.

Needless to say, a person skilled in the art will take care to select this or these optional additional compound(s) such that the advantageous properties intrinsically associated with the composition in accordance with the invention are not, or are not substantially, adversely affected by the envisaged addition(s).

The pH of the dye composition in accordance with the invention is generally between 2 and 14 approximately and preferably greater than 7, preferentially greater than 9.

It may be adjusted to the desired value by means of acidifying or basifying agents usually used in the dyeing of keratin fibres, or alternatively using standard buffer systems.

Among the acidifying agents that may be mentioned, for example, are mineral or organic acids, for instance hydrochloric acid, orthophosphoric acid or sulphuric acid, carboxylic acids, for instance acetic acid, tartaric acid, citric acid and lactic acid, and sulphonic acids.

Among the basifying agents, examples that may be mentioned include aqueous ammonia, alkali metal carbonates, alkanolamines, such as mono-, di- and triethanolamines and derivatives thereof, sodium hydroxide, potassium hydroxide and the compounds of the formula (V) below:

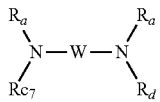

in which W is a propylene residue optionally substituted with a hydroxyl group or a $C_1$-$C_4$ alkyl radical; and $R_a$, $R_b$, $R_c$ and $R_d$, which may be identical or different, represent a hydrogen atom or a $C_1$-$C_4$ alkyl or $C_1$-$C_4$ hydroxyalkyl radical.

The composition of the invention is applied to the keratin fibres with a leave-in time generally of between 1 and 60 minutes approximately, preferably between 10 and 60 minutes approximately. After the leave-in time, the keratin fibres are usually rinsed to reveal dyed fibres.

The dye composition may contain an oxidizing agent, either for lightening the fibres or when use is made of an oxidation base and/or a coupler in the composition. The oxidizing agents conventionally used for the oxidation dyeing of keratin fibres are, for example, hydrogen peroxide, urea peroxide, alkali metal bromates, persalts such as perborates and persulphates, peracids and oxidase enzymes, among which mention may be made of peroxidases, 2-electron oxidoreductases such as uricases, and 4-electron oxygenases, for instance laccases. Hydrogen peroxide is particularly preferred.

The oxidizing agent may be added to the composition of the invention just at the time of use, or it may be used in the form of an oxidizing composition containing it, which is applied simultaneously with or sequentially to the composition of the invention. The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably ranges between 3 and 12 approximately, and more preferably still between 7 and 11, better still between 7 and 10. It may be adjusted to the desired value by means of acidifying or basifying agents usually used in the dyeing of keratin fibres and as defined above.

The composition which is ultimately applied to the keratin fibres may be in various forms, such as in the form of liquids, creams or gels, or in any other form that is suitable for dyeing keratin fibres, and especially human hair.

The examples that follow serve to illustrate the invention without, however, being limiting in nature.

EXAMPLES

Example 1

Example 1

Direct Dyeing

The following dye composition is prepared from the following ingredients in the following proportions indicated in grams of product as active material:

Dye Composition

|  | A | B | C |
|---|---|---|---|
| Dye 1 | 0.5 g | | |
| Dye 2 | | 0.5 g | |
| Dye 3 | | | 0.5 g |
| Benzyl alcohol | 5 g | 5 g | 5 g |
| Ethanol | 15 g | 15 g | 15 g |
| Hydroxyethyloleyldi-methylammonium chloride | 1.5 g | 1.5 g | 1.5 g |
| Fragrance | qs | qs | qs |
| 20% Ammonium hydroxide (expressed as ammonia) | 2.6 g | 2.6 g | 2.6 g |
| Water | qs 100 g | qs 100 g | qs 100 g |

Locks of natural and permanent-waved hair containing 90% white hair are treated for 30 minutes at room temperature with dye compositions A to C.

They are then rinsed, shampooed and dried.

The colouring is evaluated in the L*a*b* system with a CM2600D spectrophotometer.

In this system, L* represents the intensity; the lower the value of L*, the more intense the colouring obtained. The chromaticity is measured by the values a* and b*, a* representing the red/green axis and b* the yellow/blue axis.

Determination of the Dyeing Strength

The colouring obtained is evaluated by the measurement of ΔE, which is the variation of the colour before and after application of the dye, from the formula:

$$\Delta E = \sqrt{(L^*-L_o^*)^2+(a^*-a_o^*)^2+(b^*-b_o^*)^2}$$

in which $L^*$ represents the intensity and $a^*$ and $b^*$ the chromaticity of the dyed hair, and $L0^*$ represents the intensity and $a0^*$ and $b0^*$ the chromaticity of the hair before dyeing. The colour is more intense, the larger the ΔE.

Determination of the Resistance to Washing Operations

The locks dyed with the above compositions were subjected to 10 shampooing operations according to a cycle that includes wetting the locks with water, washing with shampoos, rinsing with water followed by a drying operation (Machine Star).

The colour of the locks before and after the 10 washing operations was evaluated in the $L^*a^*b^*$ system. The colour variation before and after the washing operations was measured by ΔE according to the above equation from values of $L0^*a0^*b0^*$ of the dyed locks and values of $L^*a^*b^*$ obtained after 10, respectively 30 shampooing operations.

The larger the value of Δ, the greater the difference in colour before and after washing operations, and in the present case, the less resistant the colouring is to shampooing operations.

Determination of the Lightfastness

The locks dyed with the above compositions were exposed to strong light according to the following protocol:

The dyed locks are exposed to light from a xenon lamp using a Xenotest beta machine. The exposure time is 24 hours (Irradiation: 90 W/m).

The colour of the locks before and after exposure was evaluated in the $L^*a^*b^*$ system. The colour variation before and after exposure was measured by ΔE according to the above equation from values of $L0^*a0^*b0^*$ of the dyed locks and values of $L^*a^*b^*$ obtained after exposure.

The larger the value of ΔE, the greater the difference in colour before and after exposure, and in the present case, the less lightfast the colouring. Colourings of the locks are obtained which are strong and highly resistant to shampooing operations and to UV rays.

| Composition | Hair | Colour | Uptake (ΔE) | Degradation after 10 shampooing operations (ΔE) | Degradation after strong light test (ΔE) |
|---|---|---|---|---|---|
| Composition A | Natural | Blue | 48 | 8.1 | 10.3 |
| | Permanent-waved | | 51 | 3.0 | 11.9 |
| Composition B | Natural | Violet | 48 | 10.5 | 4.1 |
| | Permanent-waved | | 48 | 1.5 | 2.7 |
| Composition C | Natural | Violet | 44 | 8.1 | 12.6 |
| | Permanent-waved | | 46 | 2.4 | 8.9 |

| | D |
|---|---|
| Dye 1 | 1.25 g |
| Benzyl alcohol | 12.5 g |
| Ethanol | 37.5 g |
| Hydroxyethyloleyldi-methylammonium chloride | 3.75 g |
| Fragrance | qs |
| 20% Ammonium hydroxide (expressed as ammonia) | 2.6 g |
| Water | qs 100 |

Composition D is mixed with a commercial 20-volume oxidizing agent (L'Oréal Professionnel Paris) in a proportion of 8 g of composition D with 12 g of oxidizing agent per lock.

The composition resulting from the mixing is applied to locks of natural and permanent-waved hair containing 90% white hair. After a leave-in time of 30 minutes at room temperature, the locks are then rinsed, shampooed and dried.

The dyeing power for the dyeing of the locks and the degradation of the colour after shampooing resistance tests (washing, rinsing, wringing and drying) are then observed.

The colouring of the hair is measured with a CM2600 D spectrophotometer. Colourings of the locks are obtained that are strong and very resistant to shampooing operations.

| Composition | Hair | Colour | Rise (ΔE) | Degradation after 10 shampooing operations (ΔE) |
|---|---|---|---|---|
| Composition D | Natural | Blue | 51.45 | 6.0 |
| | Permanent-waved | | 59.53 | 2.7 |

Example 2

Direct Dyeing

The following dye composition is prepared from the following ingredients in the following proportions indicated in grams of active material:

| | 2A | 2B | 2C |
|---|---|---|---|
| Dye 2-1 | 0.5 g | — | — |
| Dye 2-3 | — | 0.5 g | — |
| Dye 2-4 | — | — | 0.5 g |
| Benzyl alcohol | 5 g | 5 g | 5 g |
| Ethanol | 15 g | 15 g | 15 g |
| Hydroxyethyloleyldi-methylammonium chloride | 1.5 g | 1.5 g | 1.5 g |
| Fragrance | qs | qs | qs |
| Ammonium hydroxide (expressed as ammonia) | 2.6 g | 2.6 g | 2.6 g |
| Water | qs 100 g | qs 100 g | qs 100 g |

Locks of natural and permanent-waved hair containing 90% white hair are treated for 30 minutes at room temperature with dye compositions A to D.

They are then rinsed, shampooed and dried.

The colouring is evaluated in the $L^*a^*b^*$ system with a CM2600D spectrophotometer.

In this system, $L^*$ represents the intensity; the lower the value of $L^*$, the more intense the colouring obtained. The chromaticity is measured by the values $a^*$ and $b^*$, $a^*$ representing the red/green axis and $b^*$ the yellow/blue axis.

The strength of the colouring obtained is evaluated by the measurement of ΔE, which is the variation of the colour before and after application of the dye, from the formula:

$$\Delta E = \sqrt{(L^* - L_o^*)^2 + (a^* - a_o^*)^2 + (b^* - b_o^*)^2}$$

in which L* represents the intensity and a* and b* the chromaticity of the dyed hair, and L0* represents the intensity and a0* and b0* the chromaticity of the hair before dyeing. The colour is more intense, the larger the ΔE.

| Comp | Type of hair | Dyeing strength ΔE |
|---|---|---|
| 2-A | natural | 17 |
| 2-A | permanent-waved | 21 |
| 2-B | natural | 20 |
| 2-B | permanent-waved | 24 |
| 2-C | natural | 45 |
| 2-C | permanent-waved | 46 |

The colourings obtained on the hair are strong and not very selective.

Determination of the Resistance to Washing Operations

The locks dyed with the above compositions were subjected to 10, then 30 shampooing operations according to a cycle that includes wetting the locks with water, washing with shampoos, rinsing with water followed by a drying operation (Machine Star).

The colour of the locks before and after the 10 washing operations was evaluated in the L*a*b* system. The colour variation before and after the washing operations was measured by ΔE according to the equation below from values of L0*a0*b0* of the dyed locks and values of L*a*b* obtained after 10 shampooing operations.

$$\Delta E = \sqrt{(L^* - L_o^*)^2 + (a^* - a_o^*)^2 + (b^* - b_o^*)^2}$$

The larger the value of ΔE, the greater the difference in colour before and after washing operations, and in the present case, the less resistant the colouring is to shampooing operations.

| Composition | Hair | Colour | Degradation after 10 shampooing operations (ΔE) |
|---|---|---|---|
| 2A | Natural | Beige | 4.6 |
|  | Perm |  | 2.3 |
| 2B | Natural | Grey | 4.5 |
|  | Perm |  | 4.9 |
| 2C | Natural | Blue | 5.9 |
|  | Perm |  | 1.9 |

Example 3

Lightening Direct Dyeing

The following dye composition is prepared from the following ingredients in the following proportions indicated in grams:

|  | 3E | 3F | 3G |
|---|---|---|---|
| Dye 2-1 | 1.25 g | — | — |
| Dye 2-3 | — | 1.25 g | — |
| Dye 2-4 | — | — | 1.25 g |
| Benzyl alcohol | 12.5 g | 12.5 g | 12.5 g |
| Ethanol | 37.5 g | 37.5 g | 37.5 g |
| Hydroxyethyl oleyl dimonium chloride | 3.75 g | 3.75 g | 3.75 g |
| Fragrance | qs | qs | qs |
| 20% Ammonium hydroxide (expressed as ammonia) | 13 g | 13 g | 13 g |
| Water | qs 100 g | qs 100 g | qs 100 g |

Compositions 3E to 3G are mixed with a commercial 20-volume oxidizing agent (L'Oréal Professionnel Paris) in a proportion of 8 g of each of dyeing compositions D to F with 12 g of oxidizing agent per lock.

These compositions are then applied to locks of natural and permanent-waved hair containing 90% white hair. After a leave-in time of 30 minutes at room temperature, the locks are then rinsed, shampooed and dried.

The dyeing power for the dyeing of the locks and the degradation of the colour after shampooing resistance tests carried out manually (washing, rinsing, wringing and drying), according to the calculation methods of Example 1, are then observed.

The colouring of the hair is measured with a CM2600 D spectrophotometer. Colourings of the locks are obtained that are strong and very resistant to shampooing operations.

| Dye | Hair | Degradation after 10 shampooing operations (ΔE) | Dyeing strength ΔE |
|---|---|---|---|
| 3E | Natural | 2.8 | 17 |
| 3F | Natural | 6.9 | 22 |
| 3G | Natural | 3.0 | 43 |

The invention claimed is:

1. A composition for dyeing keratin fibers comprising:

benzyl alcohol;

at least one $C_1$-$C_4$ monoalcohol; and at least one direct dye chosen from formula (I), formula (II), and salts thereof:

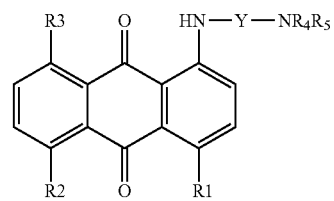

Formula I wherein Y is chosen from divalent alkylene radicals comprising from 1 to 8 carbon atoms;

$R_4$ and $R_5$, which may be identical or different, are chosen from hydrogen atoms and alkyl and hydroxyalkyl radicals comprising from 1 to 8 carbon atoms;

R1 is chosen from hydrogen atoms and hydroxyl radicals;

R2 and R3, which may be identical or different, are chosen from hydrogen atoms and $NH_2$ radicals;

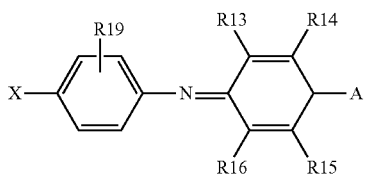

Formula (II)

wherein:

X is chosen from the groups —OH, NH$_2$, NHR$_{11}$, NHR$_{12}$ and NR$_{11}$R$_{12}$ wherein R$_{11}$ and R$_{12}$ are chosen from:
  C$_1$-C$_8$ alkyl groups, optionally substituted by a group chosen from —OH groups and amino groups substituted by a radical comprising at least one C$_6$-C$_{20}$ aromatic ring, R13, R15 and R16, which may be identical or different, are chosen from:
  hydrogen atoms;
  halogen atoms;
  hydroxyl groups;
  optionally substituted, linear and branched C$_1$-C$_8$ alkoxy and alkyl groups;

R14 is chosen from:
  hydrogen atoms;
  hydroxyl groups;
  optionally substituted, linear and branched C$_1$-C$_8$ alkoxy and alkyl groups; and
  NH$_2$ and NHR17 group wherein R17 is chosen from (C$_1$-C$_4$)alkoxycarbonylamino radicals and C$_6$-C$_{20}$ aromatic radicals optionally substituted by at least one group chosen from amino, hydroxyl, C$_1$-C$_4$ alkyl, (C$_1$-C$_4$)dialkylamino, (C$_1$-C4)alkylhydroxy(C$_1$-C$_4$)alkylamino and dihydroxy(C$_1$-C$_4$)alkylamino groups;

A is chosen from oxygen atoms, NH, and NR18 wherein R18 is chosen from C$_1$-C$_4$ alkyl radicals; and R19 is chosen from hydrogen atoms and C$_1$-C$_8$ alkyl radicals.

2. The composition according to claim 1, wherein Y is an alkylene radical comprising from 1 to 4 carbon atoms.

3. The composition according to claim 1, wherein in formula (I), R$_4$ and R$_5$, which may be identical or different, are chosen from alkyl radicals comprising from 1 to 4 carbon atoms.

4. The composition according to claim 1, wherein the amount of formula (I) ranges from about 0.001% to about 10%, by weight relative to the weight of the composition.

5. The composition according to claim 1, wherein formula (I) has a log P of greater than about 1.

6. The composition according to claim 1, wherein formula (I) is chosen from:

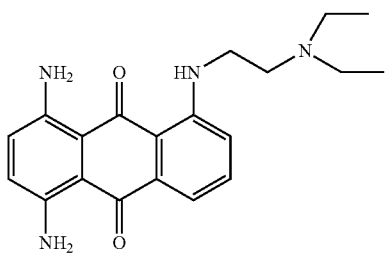

1

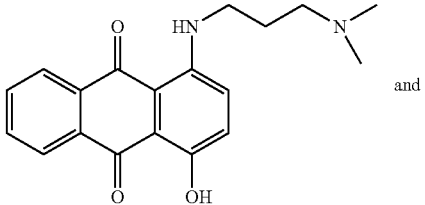

2 and

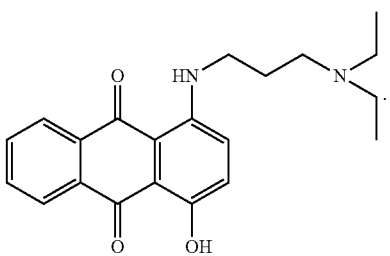

3

7. The composition according to claim 1, wherein in formula (II), R13 and R15 are hydrogen atoms.

8. The composition according to claim 1, wherein in formula (II), R16 is chosen from NH$_2$ groups; hydroxyl groups; NHR17 groups wherein R17 is a phenyl group substituted by a group chosen from amino groups, di(C1-C4)alkylamino groups, dihydroxy(C1-C4)alkylamino groups, and (C1-C4) alkylhydroxy(C1-C4)alkylamino groups; and ethoxycarbonylamino groups.

9. The composition according to claim 1, wherein in formula (II), R14 is a group chosen from alkoxy, NH$_2$, hydroxyphenylamino and aminophenylamino groups, the phenyl radical of which is optionally substituted by a C$_1$-C$_4$ alkyl.

10. The composition according to claim 1, wherein in formula (II), X is chosen from hydroxyl groups; amino groups; di(C$_1$-C$_4$)alkylamino groups; (C$_1$-C$_4$)alkylhydroxy (C$_1$-C$_4$)alkylamino groups; (C$_1$-C$_4$)alkylbenzoylamino(C$_1$-C$_4$)alkylamino groups; and dihydroxy(C$_1$-C$_4$)alkylamino groups.

11. The composition according to claim 1, wherein in formula (II), A is chosen from oxygen atoms and NH groups.

12. The composition according to claim 1, wherein in formula (II), R19 is chosen from hydrogen atoms and methyl radicals.

13. The composition according to claim 1, wherein formula (II) is chosen from:

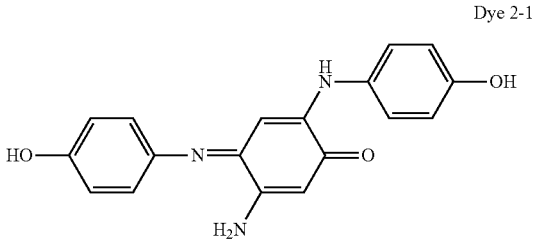

Dye 2-1

Dye 2-2
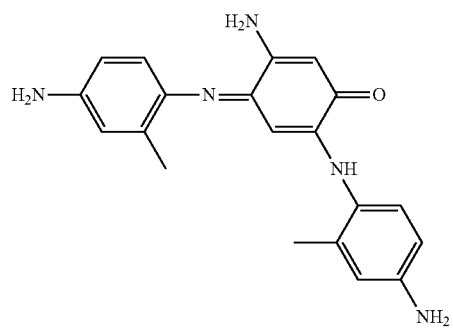
Dye 2-3
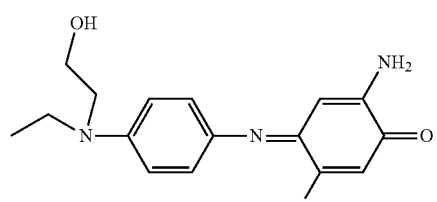
Dye 2-4
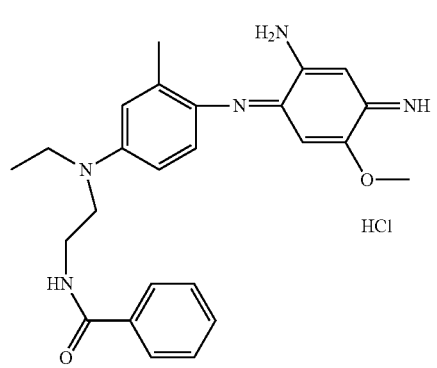
HCl
Dye 2-5
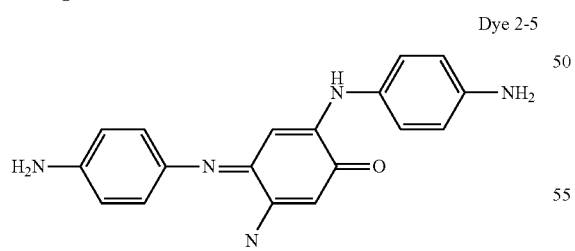
Dye 2-6
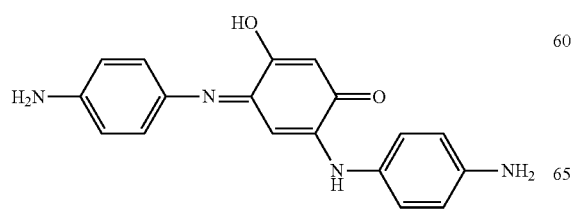
Dye 2-7
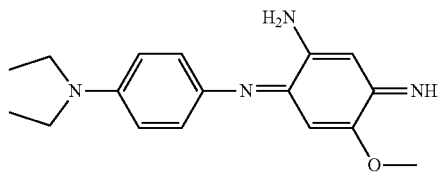
Dye 2-8
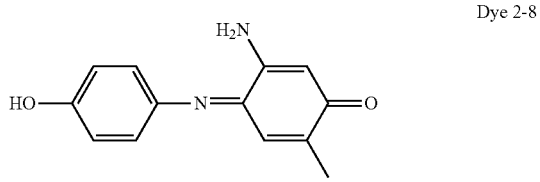
Dye 2-9
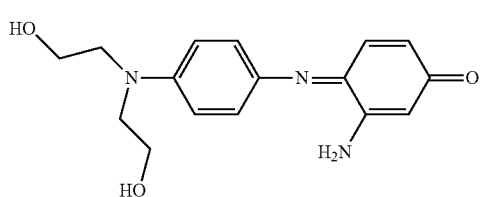
Dye 2-10
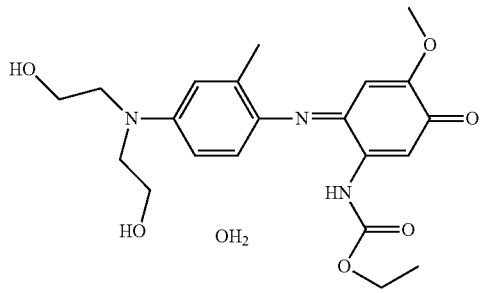
Dye 2-11
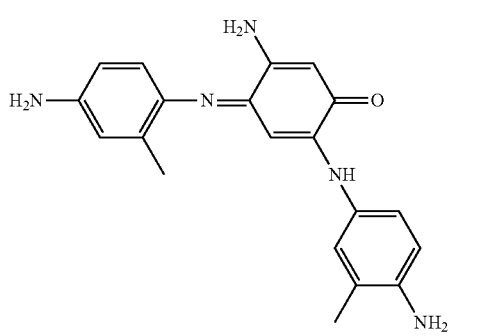
Dye 2-12
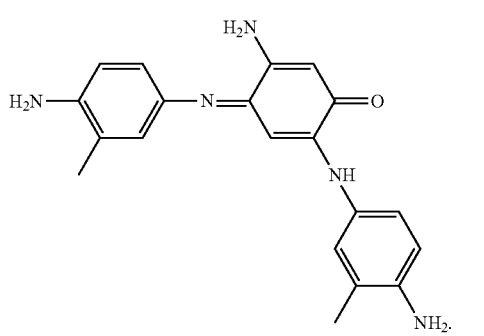

14. The composition according to claim 1, wherein the at least one $C_1$-$C_4$ monoalcohol is chosen from at least one of ethanol, isopropanol, n-propanol, and butanol.

15. The composition according to claim 1, wherein the at least one $C_1$-$C_4$ monoalcohol is present in an amount ranging from about 1% to about 30% by weight, relative to the total weight of the composition.

16. The composition according to claim 1, wherein the amount of benzyl alcohol present in the composition ranges from about 0.5% to about 8%, by weight relative to the total weight of the composition.

17. The composition according to claim 1, wherein the weight ratio of the at least one $C_1$-$C_4$ monoalcohol to the benzyl alcohol is less than or equal to about 3.5.

18. The composition according to claim 1, further comprising at least one oxidizing agent.

19. The composition according to claim 1, further comprising at least one cationic surfactant.

20. A dyeing process for dyeing human keratin fibers comprising applying to the human keratin fibers a composition comprising:
benzyl alcohol;
at least one $C_1$-$C_4$ monoalcohol; and
at least one direct dye chosen from formula (I), formula (II), and salts thereof:

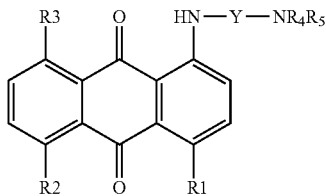

Formula I wherein Y is chosen from divalent alkylene radicals comprising from 1 to 8 carbon atoms;
$R_4$ and $R_5$, which may be identical or different, are chosen from hydrogen atoms and alkyl and hydroxyalkyl radicals comprising from 1 to 8 carbon atoms;
R1 is chosen from hydrogen atoms and hydroxyl radicals;
R2 and R3, which may be identical or different, are chosen from hydrogen atoms and $NH_2$ radicals;

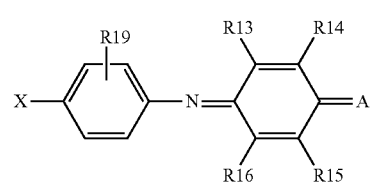

Formula (II)

wherein:
X is chosen from the groups —OH, $NH_2$, $NHR_{11}$, $NHR_{12}$ and $NR_{11}R_{12}$ wherein $R_{11}$ and $R_{12}$ are chosen from:
$C_1$-$C_8$ alkyl groups, optionally substituted by a group chosen from —OH groups and amino groups substituted by a radical comprising at least one $C_6$-$C_{20}$ aromatic ring,
R13, R15 and R16, which may be identical or different, are chosen from:
hydrogen atoms;
halogen atoms;
hydroxyl groups;
optionally substituted, linear and branched $C_1$-$C_8$ alkoxy and alkyl groups;
R14 is chosen from:
hydrogen atoms;
hydroxyl groups;
optionally substituted, linear and branched $C_1$-$C_8$ alkoxy and alkyl groups; and
$NH_2$ and NHR17 group wherein R17 is chosen from ($C_1$-$C_4$)alkoxycarbonylamino radicals and $C_6$-$C_{20}$ aromatic radicals optionally substituted by at least one group chosen from amino, hydroxyl, $C_1$-$C_4$ alkyl, ($C_1$-$C_4$)dialkylamino, ($C_1$-C4)alkylhydroxy($C_1$-$C_4$) alkylamino and dihydroxy($C_1$-$C_4$)alkylamino groups;
A is chosen from oxygen atoms, NH, and NR18 wherein R18 is chosen from $C_1$-$C_4$ alkyl radicals; and
R19 is chosen from hydrogen atoms and $C_1$-$C_8$ alkyl radicals.

21. The composition according to claim 1, wherein the weight ratio of the at least one $C_1$-$C_4$ monoalcohol to the benzyl alcohol is less than or equal to about 6.

* * * * *